US011089990B2

(12) United States Patent
Govari

(10) Patent No.: US 11,089,990 B2
(45) Date of Patent: *Aug. 17, 2021

(54) FAST RECOVERY OF ECG SIGNAL METHOD AND APPARATUS

(71) Applicant: Biosense Webster (Israel) Ltd., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 159 days.

This patent is subject to a terminal disclaimer.

(21) Appl. No.: 16/590,848

(22) Filed: Oct. 2, 2019

(65) Prior Publication Data

US 2020/0029844 A1  Jan. 30, 2020

Related U.S. Application Data

(63) Continuation of application No. 15/827,007, filed on Nov. 30, 2017, now Pat. No. 10,485,439.

(51) Int. Cl.
A61B 5/316 (2021.01)
A61B 5/00 (2006.01)
A61B 5/30 (2021.01)
A61B 5/287 (2021.01)

(52) U.S. Cl.
CPC .......... A61B 5/316 (2021.01); A61B 5/30 (2021.01); A61B 5/7217 (2013.01); A61B 5/287 (2021.01)

(58) Field of Classification Search
CPC .......... A61B 5/287; A61B 5/30; A61B 5/316; A61B 5/7217
See application file for complete search history.

(56) References Cited

U.S. PATENT DOCUMENTS

| 5,205,294 A | 4/1993 | Flach |
| 5,606,320 A | 2/1997 | Kleks |
| 5,682,902 A | 11/1997 | Herleikson |
| 6,904,315 B2 | 6/2005 | Panken |
| 2005/0149134 A1 | 7/2005 | McCabe |
| 2007/0216562 A1 | 9/2007 | Teo |
| 2009/0079606 A1 | 3/2009 | Terry |
| 2009/0177046 A1* | 7/2009 | Zhang ............... A61B 5/0002 600/300 |

FOREIGN PATENT DOCUMENTS

WO   2013/103353 A1   7/2013

OTHER PUBLICATIONS

Extended European Search Report dated Mar. 1, 2019 for the European Patent Application No. 18209055.5.

* cited by examiner

Primary Examiner — George Manuel
(74) Attorney, Agent, or Firm — Volpe Koenig

(57) ABSTRACT

Fast recovery electrocardiogram (ECG) signal method and apparatus are provided. In one embodiment, an ECG apparatus includes an input for receiving a biometric cardiogram signal, such as a Wilson Central Terminal (WCT) signal, and a combiner, such as an adder, for producing a compensated signal. Processing circuitry produces an ECG reflective of the compensated signal and also outputs a signal corresponding to high frequency response of the compensated signal to compensate for low response of the biometric cardiogram signal to high frequency spikes. A resultant ECG is produced by the processing circuitry having pacing signal contribution within the biometric cardiogram signal cancelled.

18 Claims, 3 Drawing Sheets

FAST RECOVERY OF ECG SIGNAL METHOD AND APPARATUS

CROSS REFERENCE TO RELATED APPLICATION

This application is a continuation of U.S. patent application Ser. No. 15/827,007, filed Nov. 30, 2017, which is incorporated by reference as if fully set forth.

SUMMARY

Fast recovery electrocardiogram (ECG) signal method and apparatus are provided. In one embodiment, an ECG apparatus includes an input for receiving a biometric cardiogram signal of a patient and a compensation signal combiner for selectively producing a compensated biometric cardiogram signal of the biometric cardiogram signal of the patient.

Processing circuitry is provided that includes an analog to digital converter, a digital processor and a digital to analog converter. The analog to digital converter provides a digitized version of the compensated biometric cardiogram signal to the digital processor. The digital processor produces an ECG reflective of the compensated biometric cardiogram signal and also outputs a digital signal corresponding to high frequency response of the digitized compensated biometric cardiogram signal to the digital to analog converter. The digital to analog converter provides an analog version of the digital signal corresponding to high frequency response of the digitized compensated biometric cardiogram signal to the compensation signal combiner to compensate for low response of the biometric cardiogram signal of the patient to high frequency spikes. A resultant ECG is produced by the digital processor having pacing signal contribution within the biometric cardiogram signal cancelled.

Preferably, the input is configured to receive a Wilson Central Terminal (WCT) biometric cardiogram signal of a patient. Also, the compensation signal combiner is in one embodiment an adder. The compensated biometric cardiogram signal of the biometric cardiogram signal of the patient can be combined via an operational amplifier with an intra cardiac signal in a differential amplifier configuration as the input to the analog to digital converter. The processor can be configured to produce the ECG reflective of the compensated biometric cardiogram signal in a graph form reflecting microvolts of signal over time in tenths of seconds.

In another embodiment, a method of producing an electrocardiogram (ECG) is provided. A biometric cardiogram signal of a patient is received. A compensated biometric cardiogram signal of the biometric cardiogram signal of the patient is selectively produced. A digitized version of the compensated biometric cardiogram signal is provided to a digital processor. The digital processor produces an ECG reflective of the compensated biometric cardiogram signal and outputs a digital signal corresponding to high frequency response of the digitized compensated biometric cardiogram signal to a digital to analog converter. The digital to analog converter providing an analog version of the digital signal corresponding to high frequency response of the digitized compensated biometric cardiogram signal that is combined with the biometric cardiogram signal to compensate for low response of the biometric cardiogram signal of the patient to high frequency spikes. A resultant ECG is produced by the digital processor having pacing signal contribution within the biometric cardiogram signal cancelled.

Preferably, a Wilson Central Terminal (WCT) biometric cardiogram signal is received as the biometric cardiogram signal of the patient. Also, the analog version of the digital signal corresponding to high frequency response of the digitized compensated biometric cardiogram signal is in one embodiment added to biometric cardiogram signal produce the compensated biometric cardiogram signal.

The compensated biometric cardiogram signal of the biometric cardiogram signal of the patient can be combined via an operational amplifier with an intra cardiac signal in a differential amplifier configuration as the input to an analog to digital converter which provides the digitized version of the compensated biometric cardiogram signal to the digital processor. The processor can produce the ECG reflective of the compensated biometric cardiogram signal in a graph form reflecting microvolts of signal over time in tenths of seconds.

Other object and advantages of the invention will be apparent to those skilled in the art from the drawings and following detailed description.

DETAILED DESCRIPTION OF THE PREFERRED EMBODIMENT(S)

The present invention is related to ECG systems and methods. The inventors have recognized that electrophysiology physicians require an enhanced ECG system that compensates for the interfering signals caused by pacing.

ECG monitoring systems that include pace pulse detection are known in the art. For example, see U.S. Pat. No. 5,682,902 (Herleikson). Such standard ECG input systems utilize analog to digital signal processing. Pacing signals can be detected through the analysis of the digital signals. In conventional ECG systems, such as Herleikson, pace pulse signals can be removed though replacement with a selected flat signal for a specified or calculated time. The inventors have recognized that electrophysiology physicians can benefit from an enhanced ECG system that more accurately compensates for the interfering signals caused by pacing.

Figure 1:
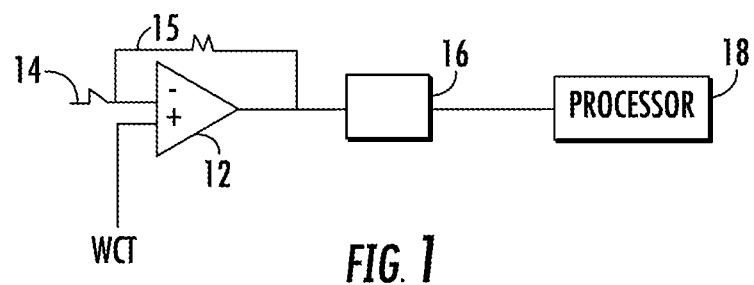
FIG. 1 is a schematic illustration of an ECG system based on conventional teachings.

Consistent with the conventional methodology, an ECG system 10 can be constructed, for example, to process Wilson Central Terminal ("WCT") ECG signals of a patient that average three active limb electrode voltages measured with respect to a return ground electrode. As illustrated in FIG. 1, a WCT signal can be combined via an operational amplifier 12 with an intra cardiac signal 14 in a differential amplifier configuration 15 as the input to an analog to digital converter 16. The digital output of the analog to digital converter 16 is then processed by a processor 18 in a conventional manner, such as corresponding to the processing taught by Herleikson, to produce an ECG corresponding to the WCT signal.

When the WCT signal includes a pacing charge, however, the ECG produced by the system 10 that uses conventional processing of the digitized signal, is partially skewed due to conventional processing of the pacing signal.

Figure 2:
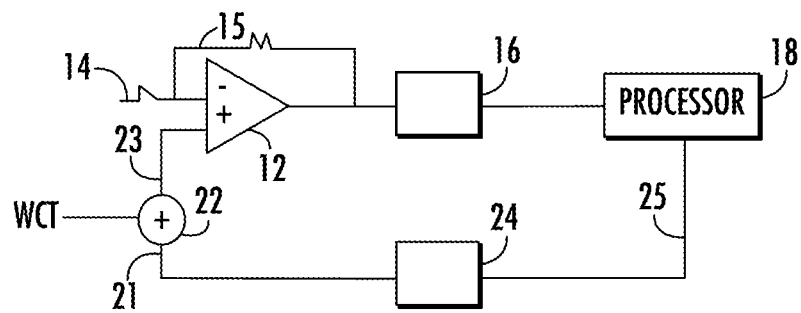
FIG. 2 is a schematic illustration of an ECG system in accordance with the teachings of the present invention.

The present invention provides an improved ECG system that implements a digital to analog compensation value to cancel out the pacing charge such that a more accurate ECG is produced. Referring to FIG. 2, an example fast-recovery ECG input system 20 is provided that utilizes an analog to digital converter 16 and associated processor 18 to detect pacing, similar to the system 10 of FIG. 1. However, the processor 18 of the FIG. 2 modified system 20 is configured to process the WCT signal after being combined with an added DC value signal 21 that cancels out the pacing charge when the WTC signal includes a pacing charge.

Applicants have recognized that when a pacing signal is applied, the WTC signal will include both significant low and high frequency components that arise from the electronic pacing pulse. As illustrated in FIG. 2, the WTC signal is passed through an adder 22 which adds the cancellation signal 21 to compensate for the low response of the WTC signal to high frequency spikes. The post-adder "compensated" WTC signal 23 is provided to the analog to digital converter 16 via the operational amplifier 12 with an intra cardiac signal 14 in a differential amplifier configuration 15. The digital output of the analog to digital converter 16 is then provided to a digital processor 18.

The digital output of the analog to digital converter 16 is processed by the processor 18 in a conventional manner, such as corresponding to the processing taught by Herleikson, to produce an ECG corresponding to the compensated WCT signal. Additionally, however, a high frequency response of the digital signal received from the analog to digital converter 16 is used by the processor 18 to create a digital compensation signal 25. The digital compensation signal 25 is passed through a digital to analog converter 24 to provide the analog signal 21 which is added to the WTC signal. The result of adding the cancellation signal 21 to the WTC signal causes the processor 18 to produce an ECG having the pacing signal contribution within the biometric cardiogram signal cancelled since the ECG is based on the compensated WTC signal 23.

The high frequency response of the WTC signal, which is significant when the WTC signal includes a pacing pulse, is determined by the processor 18 to produce the digital compensation signal 25 that is fed to the digital to analog converter 24 to provide the compensation signal 21 which is added to the WTC signal. Once a pacing artifact is detected by the processor 18, a short averaging window can be used to keep the signal always without an offset. The digital compensation signal 25 input to the digital to analog converter 24 is smoothed to avoid steps.

Figure 3A:
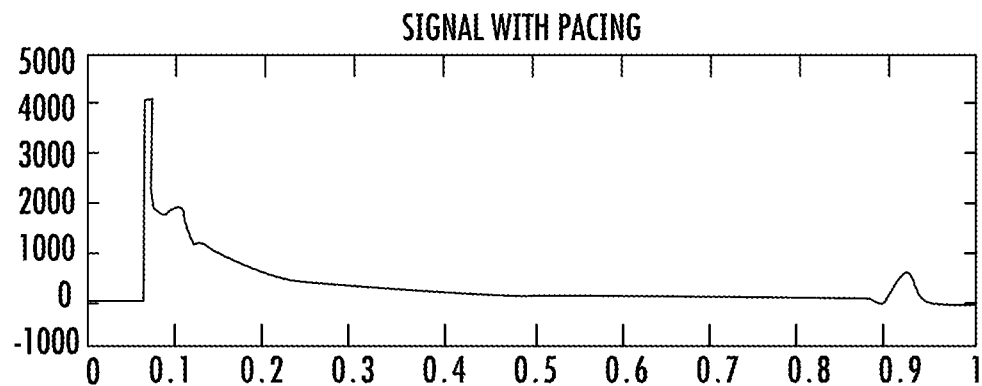
FIGS. 3(A)-3(C) are illustrations of ECG related signals.
Figure 3B:
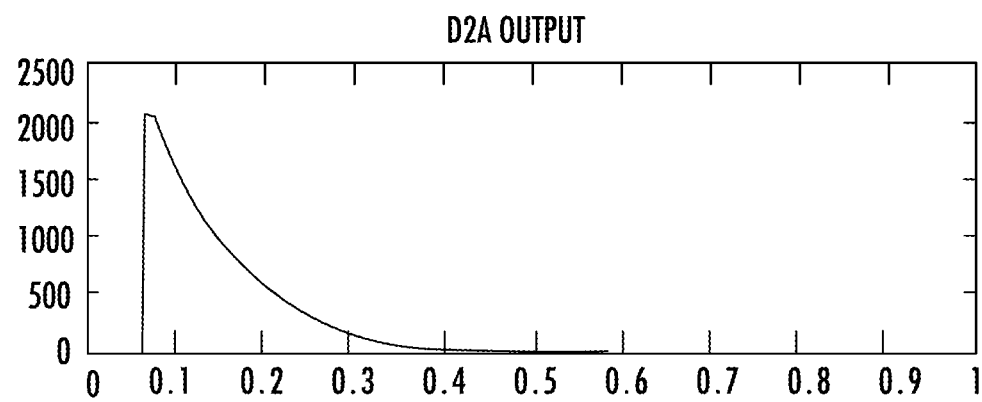
Figure 3C:
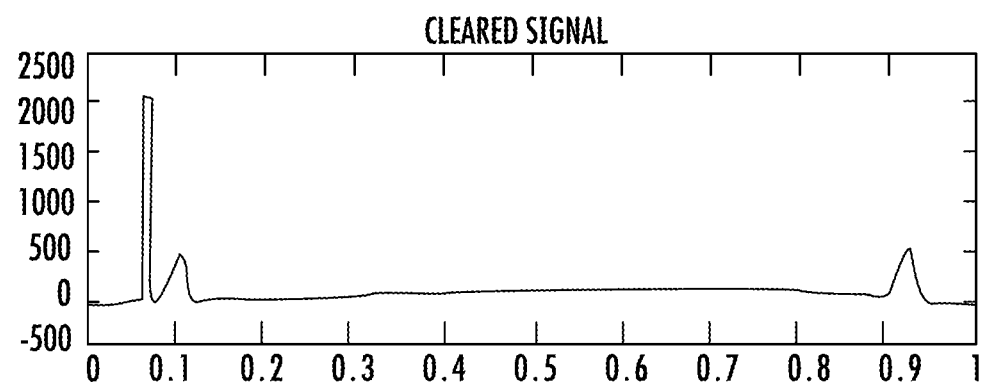

The resultant ECG signal graphs both with and without having the cancellation signal applied are illustrated in FIGS. 3A and C. FIG. 3A reflects the WTC signal without cancellation and FIG. 3C illustrates the resultant ECG that utilizes the pace pulse cancellation of the fast-recovery ECG input system 20. For reference, FIG. 3B is provided that reflects an ECG channel response to a pace pulse signal within the WTC signal. The graphs reflect microvolts (µVs) of signal over one second of time.

Figure 4:
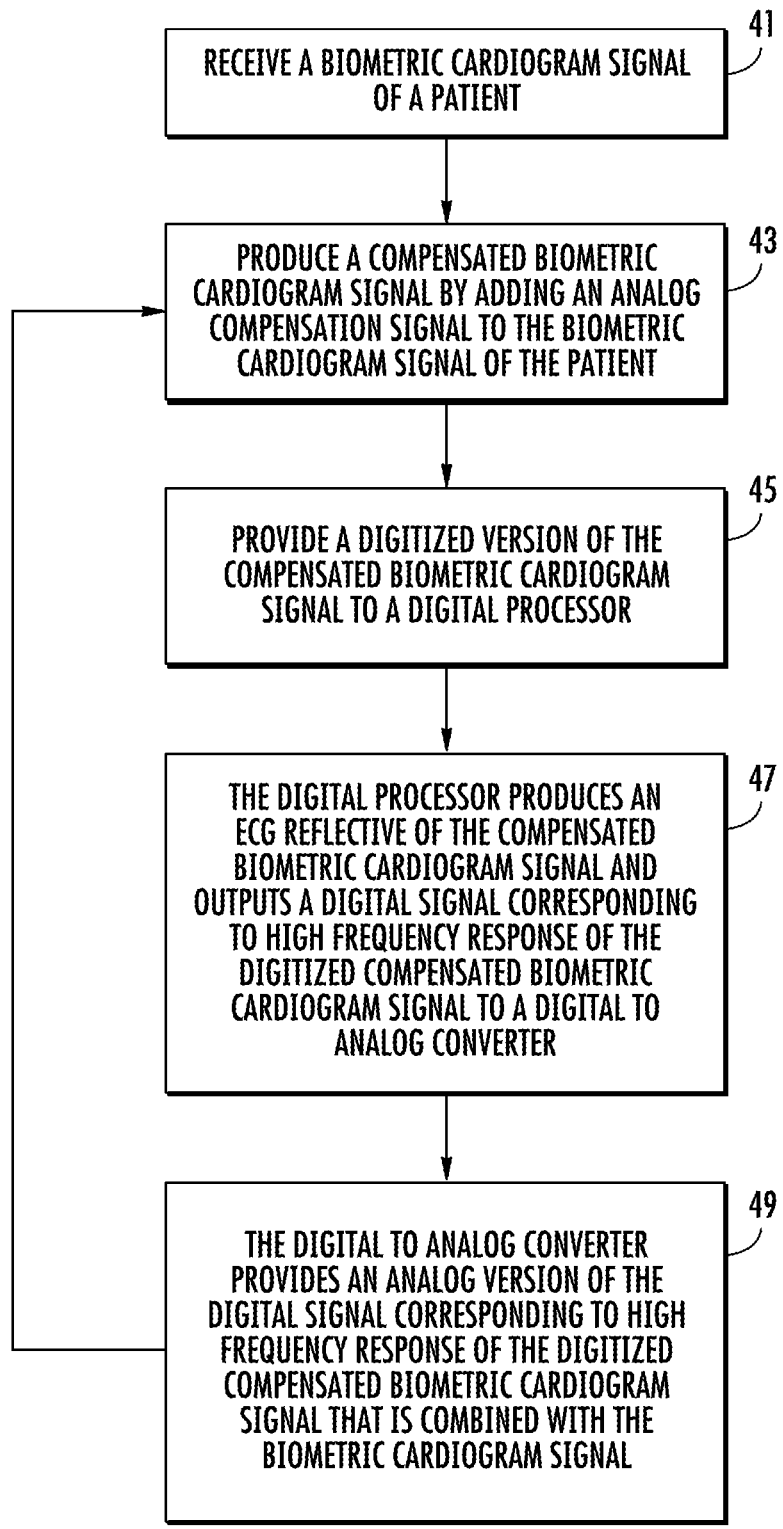
FIG. 4 is a flow diagram of a method of producing an electrocardiogram (ECG) in accordance with the teachings of the present invention.

With reference to FIG. 4, An example method of producing the ECG depicted in FIG. 3C is provided. In step 41, a biometric cardiogram signal of a patient is received. In step 43, a compensated biometric cardiogram signal is produced by adding an analog compensation signal to the biometric cardiogram signal of the patient. In step 45, a digitized version of the compensated biometric cardiogram signal is provided to a digital processor. In step 47, the digital processor produces an ECG reflective of the compensated biometric cardiogram signal and outputs a digital signal corresponding to high frequency response of the digitized compensated biometric cardiogram signal to a digital to analog converter. In step 49, the digital to analog converter provides an analog version of the digital signal corresponding to high frequency response of the digitized compensated biometric cardiogram signal that is combined with the biometric cardiogram signal in step 43 to compensate for low response of the biometric cardiogram signal of the patient to high frequency spikes whereby an ECG is produced by the digital processor having pacing signal contribution within the biometric cardiogram signal cancelled.

All references cited in this application are incorporated by reference herein as if fully set forth. It will be apparent to one of ordinary skill in the art that many changes and modifications can be made to the embodiments described without departing from the spirit or scope of the invention as set forth herein.

What is claimed is:

1. An electrocardiogram (ECG) apparatus comprising:
an input configured to receive a Wilson Central Terminal (WCT) biometric cardiogram signal of a patient;
a compensation signal combiner for selectively producing a compensated biometric cardiogram signal of the biometric cardiogram signal of the patient; and
processor circuitry configured to receive the compensated biometric cardiogram signal and to produce an ECG reflective of the compensated biometric cardiogram signal and to output a signal corresponding to high frequency response of the compensated biometric cardiogram signal to the compensation signal combiner to compensate for low response of the biometric cardiogram signal of the patient to high frequency spikes whereby an ECG is produced by the processor circuitry having pacing signal contribution within the biometric cardiogram signal cancelled.

2. The ECG apparatus according to claim 1 wherein the compensation signal combiner is an adder.

3. The ECG apparatus according to claim 2 wherein the compensated biometric cardiogram signal of the biometric cardiogram signal of the patient is combined via an operational amplifier with an intra cardiac signal in a differential amplifier configuration to produce a combined compensated biometric cardiogram signal that is received by the processor circuitry.

4. The ECG apparatus according to claim 3 wherein the processor circuitry is configured to produce the ECG reflective of the compensated biometric cardiogram signal in a graph form reflecting microvolts of signal over time in tenths of seconds.

5. The ECG apparatus according to claim 3 wherein the processor circuitry includes:
an analog to digital converter configured to receive the combined compensated biometric cardiogram signal;
a digital processor coupled to the analog digital converter and configured to produce the ECG reflective of the compensated biometric cardiogram signal; and
a digital to analog converter coupled to the digital processor and configured to output the signal corresponding to high frequency response of the compensated biometric cardiogram signal.

6. An electrocardiogram (ECG) apparatus comprising:
an input configured to receive a biometric cardiogram signal of a patient;
a compensation signal combiner for selectively producing a compensated biometric cardiogram signal of the biometric cardiogram signal of the patient; and processor circuitry configured to produce an ECG reflective of the compensated biometric cardiogram signal and to output a signal corresponding to high frequency response of the compensated biometric cardiogram signal to the compensation signal combiner to compensate for low response of the biometric cardiogram signal of the patient to high frequency spikes whereby an ECG is produced by the processor circuitry having pacing signal contribution within the biometric cardiogram signal cancelled;

wherein the compensated biometric cardiogram signal of the biometric cardiogram signal of the patient is combined via an operational amplifier with an intra cardiac signal in a differential amplifier configuration to produce a combined compensated biometric cardiogram signal that is received by the processor circuitry.

7. The ECG apparatus according to claim 6 wherein the compensation signal combiner is an adder.

8. The ECG apparatus according to claim 7 wherein the processor circuitry is configured to produce the ECG reflective of the compensated biometric cardiogram signal in a graph form reflecting microvolts of signal over time in tenths of seconds.

9. The ECG apparatus according to claim 7 wherein the processor circuitry includes:
   an analog to digital converter configured to receive the combined compensated biometric cardiogram signal;
   a digital processor coupled to the analog digital converter and configured to produce the ECG reflective of the compensated biometric cardiogram signal; and
   a digital to analog converter coupled to the digital processor and configured to output the signal corresponding to high frequency response of the compensated biometric cardiogram signal.

10. A method of producing an electrocardiogram (ECG) comprising:
   receiving a Wilson Central Terminal (WCT) biometric cardiogram signal of a patient;
   selectively producing a compensated biometric cardiogram signal of the biometric cardiogram signal of the patient;
   providing the compensated biometric cardiogram signal to processor circuitry; and
   the processor circuitry producing an ECG reflective of the compensated biometric cardiogram signal and outputting a signal corresponding to high frequency response of the compensated biometric cardiogram signal that is combined with the biometric cardiogram signal to compensate for low response of the biometric cardiogram signal of the patient to high frequency spikes whereby an ECG is produced by the processor circuitry having pacing signal contribution within the biometric cardiogram signal cancelled.

11. The method according to claim 10 wherein the signal corresponding to high frequency response of the compensated biometric cardiogram signal is added to biometric cardiogram signal to produce the compensated biometric cardiogram signal.

12. The method according to claim 11 wherein the compensated biometric cardiogram signal of the biometric cardiogram signal of the patient is combined via an operational amplifier with an intra cardiac signal in a differential amplifier configuration to produce a combined compensated biometric cardiogram signal that is received by the processor circuitry.

13. The method according to claim 12 wherein the processor circuitry produces the ECG reflective of the compensated biometric cardiogram signal in a graph form reflecting microvolts of signal over time in tenths of seconds.

14. The method according to claim 12 where the processor circuitry includes an analog to digital converter, a digital processor coupled to the analog digital converter, and a digital to analog converter coupled to the digital processor wherein:
   the analog to digital converter receives the combined compensated biometric cardiogram signal;
   the digital processor produces the ECG reflective of the compensated biometric cardiogram signal in a graph form; and
   the digital to analog converter outputs the signal corresponding to high frequency response of the compensated biometric cardiogram signal.

15. A method of producing an electrocardiogram (ECG) comprising:
   receiving a biometric cardiogram signal of a patient;
   selectively producing a compensated biometric cardiogram signal of the biometric cardiogram signal of the patient;
   providing the compensated biometric cardiogram signal to processor circuitry; and
   the processor circuitry producing an ECG reflective of the compensated biometric cardiogram signal and outputting a signal corresponding to high frequency response of the compensated biometric cardiogram signal that is combined with the biometric cardiogram signal to compensate for low response of the biometric cardiogram signal of the patient to high frequency spikes whereby an ECG is produced by the processor circuitry having pacing signal contribution within the biometric cardiogram signal cancelled;

wherein the compensated biometric cardiogram signal of the biometric cardiogram signal of the patient is combined via an operational amplifier with an intra cardiac signal in a differential amplifier configuration to produce a combined compensated biometric cardiogram signal that is received by the processor circuitry.

16. The method according to claim 15 wherein the signal corresponding to high frequency response of the compensated biometric cardiogram signal is added to biometric cardiogram signal to produce the compensated biometric cardiogram signal.

17. The method according to claim 16 wherein the processor circuitry produces the ECG reflective of the compensated biometric cardiogram signal in a graph form reflecting microvolts of signal over time in tenths of seconds.

18. The method according to claim 16 where the processor circuitry includes an analog to digital converter, a digital processor coupled to the analog digital converter, and a digital to analog converter coupled to the digital processor wherein:
   the analog to digital converter receives the combined compensated biometric cardiogram signal;
   the digital processor produces the ECG reflective of the compensated biometric cardiogram signal in a graph form; and
   the digital to analog converter outputs the signal corresponding to high frequency response of the compensated biometric cardiogram signal.

* * * * *